(12) United States Patent
Bacher

(10) Patent No.: US 8,114,017 B2
(45) Date of Patent: Feb. 14, 2012

(54) ARTICULATING ENDOSCOPIC INSTRUMENT

(75) Inventor: Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 1557 days.

(21) Appl. No.: 11/253,834

(22) Filed: Oct. 19, 2005

(65) Prior Publication Data

US 2006/0111609 A1    May 25, 2006

(30) Foreign Application Priority Data

Oct. 19, 2004 (DE) .......................... 10 2004 052 204

(51) Int. Cl.
*A61B 17/94* (2006.01)

(52) U.S. Cl. ........................................ 600/204; 606/205

(58) Field of Classification Search .................. 600/201, 600/204, 208, 214, 215, 217, 218, 219, 224, 600/225, 228, 244, 210, 216, 141–142; 606/83, 606/90, 105, 51, 205; 623/24, 57, 62
See application file for complete search history.

(56) References Cited

U.S. PATENT DOCUMENTS

| | | | | |
|---|---|---|---|---|
| 4,203,430 A | * | 5/1980 | Takahashi | 600/149 |
| 4,599,998 A | * | 7/1986 | Castillo | 602/16 |
| 4,944,741 A | | 7/1990 | Hasson | 606/206 |
| 5,293,863 A | * | 3/1994 | Zhu et al. | 600/214 |
| 5,350,391 A | | 9/1994 | Iacovelli | 606/170 |
| 5,368,592 A | * | 11/1994 | Stern et al. | 606/33 |
| 5,423,854 A | * | 6/1995 | Martin et al. | 606/205 |
| 5,514,157 A | * | 5/1996 | Nicholas et al. | 606/206 |
| 5,549,636 A | * | 8/1996 | Li | 606/206 |
| 5,549,637 A | | 8/1996 | Crainich | 606/207 |
| 5,827,323 A | * | 10/1998 | Klieman et al. | 606/205 |

(Continued)

FOREIGN PATENT DOCUMENTS

DE    198 40 880    3/2000

(Continued)

OTHER PUBLICATIONS

European Search Report; Jan. 20, 2006; 5 pages.

*Primary Examiner* — Thomas C. Barrett
*Assistant Examiner* — Christian Sevilla
(74) *Attorney, Agent, or Firm* — St. Onge Steward Johnston & Reens LLC

(57) ABSTRACT

An endoscopic instrument comprises a shaft, comprising a proximal end and a distal end. A grip comprising a handle is arranged at said proximal end of said shaft and a tool having at least an open and a closed position is arranged at said distal end of said shaft. Said shaft comprises at least two sections, a first section and a second section, which can be articulated with respect to said first section. Said second section comprises said tool. Said instrument further comprises an actuating element, by means of which said handle is in operative connection with said second section and with which an articulation of said second section can be initiated. Said first section or said actuating element and said tool are connected by a control element, by means of which said tool can be moved back and forth between said closed position and said open position in the course of an articulation of said second section, such that both the articulation of said second section and an opening/closing of said tool can be accomplished by the movement of said actuating element.

18 Claims, 12 Drawing Sheets

U.S. PATENT DOCUMENTS

| | | | | |
|---|---|---|---|---|
| 5,906,629 A | * | 5/1999 | Oren et al. | 606/205 |
| 6,264,637 B1 | * | 7/2001 | Hogan | 604/191 |
| 6,506,208 B2 | * | 1/2003 | Hunt et al. | 606/205 |
| 6,673,092 B1 | * | 1/2004 | Bacher | 606/205 |

FOREIGN PATENT DOCUMENTS

| | | |
|---|---|---|
| EP | 0 582 295 B1 | 1/1999 |
| WO | WO 94/21179 | 9/1994 |
| WO | WO 03/094744 | 11/2003 |

* cited by examiner

ARTICULATING ENDOSCOPIC INSTRUMENT

RELATED APPLICATION

This application claims priority of German Patent Application No. 10 2004 052 204.9 filed on Oct. 19, 2004.

FIELD OF THE INVENTION

The invention relates to an endoscopic instrument having a shaft, comprising a proximal end and a distal end, a grip comprising a handle being arranged at the proximal end of the shaft and a tool having at least an open position and a closed position, the tool being arranged at the distal end of the shaft, the shaft comprising at least two sections, a first section and a second section, which can be articulated with respect to the first section, the second section comprising the tool, the instrument further comprising an actuating element, by means of which the handle is in operative connection with the second section whereby an articulation of the second section can be initiated with said actuating element.

An endoscopic instrument of this type is known for example from EP 0 582 295 B1.

Such endoscopic instruments are used in minimally invasive surgery. This involves introducing surgical instruments into the body of a patient via small incisions under visual control through an endoscope, in order to perform manipulations there. The fact that, in minimally invasive surgery, the operating site no longer has to be completely exposed means that much smaller incisions are necessary, and consequently it is far less stressful for the patient. This reduces the time which a patient has to stay in hospital and sometimes even makes a stay in hospital superfluous. Furthermore, the possibility of pathogens getting into the patient's body is less. Consequently, with the aid of minimally invasive surgery it is possible nowadays for operations which previously necessitated a sometimes lengthy stay in hospital to be carried out on an outpatient basis.

To make an insertion through a small incision possible, such endoscopic instruments generally have an elongated form, with a cross section that is as small as possible.

However, it has been found that the possibilities for the use of such instruments are restricted, since an elongated instrument can only reach a restricted area around its distal end. Areas which are for example located at an angle of 90° from the instrument cannot be reached. It is also not possible with such an instrument to reach around an obstacle.

Consequently, it is desirable for such an endoscopic instrument to have a section which can be articulated with respect to the endoscope. In this way it is possible for example to reach sites which lie behind an organ without this having the effect that the cross section of the endoscope is enlarged when it is inserted.

Furthermore, the endoscopic instruments comprise tools at their distal end with which manipulations can be carried out in the patient's body. These instruments often have an open position and a closed position. The closed position may serve for example for minimizing the cross section of the instrument when it is inserted into the patient's body or serve the purpose of masking blades located on the tools when they are inserted into the patient's body, in order to avoid injuries.

Such endoscopic instruments may be used for example as so-called retractors. They thereby serve the purpose of moving an organ, for example the liver, in the patient's body, so that the rear side of the organ can be investigated with the aid of an endoscope.

In the case of such a retractor, both an articulation of a section of the shaft and the opening and closing of the tool are important. The articulation of a section of the shaft serves the purpose of placing the tool behind the organ, so that it can be moved.

The opening and closing of the tool serves the purpose of forming a cross section that is as small as possible in the closed state during insertion, while in the open position it serves as a retractor, to offer the largest possible supporting surface for the organ, in order to distribute the force applied over an area that is as large as possible. As a result, injuries to the organ by the instrument are minimized.

The interface between the first section and the second section may assume any form that creates a connection which can articulate in at least one direction. Examples of such connections are swivel pins, helical springs, hinges or combinations thereof.

The grip and the handle may be configured in any form known from the prior art. The grip may be configured as a pistol grip, scissors grip, as a rod-shaped grip or in any form that allows manipulation of the instrument. The handle may for example take the shape of a scissors grip, a pulling or pushing element or a rotary knob, while the shape of the grip should be taken into consideration when designing the handle.

Such endoscopic instruments are known for example from EP 0 582 295 B1. This document shows various endoscopic instruments which have an elongated shaft with a first section and a second section, which can be articulated with respect to the first section.

Furthermore, tools with an open position and a closed position are arranged at the distal end of the shaft. These tools are arranged on the second section.

Furthermore, there is an operative connection between the second section and an adjusting element arranged on the grip.

In the cases shown in this document, however, it is not the second section that is connected to the handle, but the tool. The second section is connected to a second actuating element, that is to say the articulation of the articulating section and the opening and closing of the tool take place by means of two different drives.

It follows from this arrangement that these endoscopic instruments cannot be used in a one-handed operation. However, this is often desirable, so that an operator has the second hand free, for example to adjust an endoscope for visual control.

Furthermore, it has been found that it is often difficult to coordinate the articulation of the second section and the opening and closing of the tools with two hands.

The instruments known from this document are also mechanically complex on account of the two drives that are present, the large number of components required being evident from the exploded drawings that are shown in this document.

Such mechanical complexity makes these instruments cost-intensive to produce. Furthermore, disassembly, for example for cleaning purposes, is complicated and, because of the many individual parts engaging in one another, there are a large number of gaps and niches into which body fluids, bacteria or other contaminants can penetrate.

It is therefore the object of the invention to provide an endoscopic instrument in which both the articulation of the second section and the opening and closing of the tool can be accomplished with a single drive. This would allow such an instrument to be used in one-handed operation.

Furthermore, this would make a uniform, coordinated articulation of the second section and opening and closing of the tool possible.

Furthermore, such an instrument should be as mechanically simple as possible.

SUMMARY OF THE INVENTION

According to the invention the object is achieved by providing that, in the endoscopic instrument, the first section or the actuating element and the tool are connected by a control element having a first and a second end, by means of which control element the tool can be moved back and forth between the closed position and the open position in a course of an articulation of the second section, such that both a simultaneous articulation of the second section and a movement between the open position and the closed position of the tool can be accomplished by the movement of the actuating element.

The measure stated above achieves the effect that the articulation of the second section and the opening and closing of the tool are coupled to each other. Consequently, both movements can be accomplished by a single drive. This provides an endoscopic instrument with an articulated section and a tool with at least one open position and one closed position which can be used in one-handed operation.

The connection of the first section or the actuating element and the tool by means of a control element also ensures that the articulation of the second section and the opening and closing of the tool take place as a coordinated movement.

The fact that the endoscopic instrument according to the invention now has only one drive means that it also has far fewer components than an endoscopic instrument according to the prior art. Consequently, an instrument according to the invention is less costly to produce and simpler to disassemble, for example for cleaning.

Furthermore, since only one actuating element is required, the cross section of the shaft of the instrument, in which the actuating element runs, can be kept smaller.

The control element can in this case be designed both as a single component and as a subassembly made up of components. If the control element is a single component, it may be for example a control rod or cable pull. Interengaging gear wheels or combinations of gear wheels and toothed racks may be used for example as the subassembly.

In an embodiment of the invention, the control element is designed as a control rod.

A control rod has the advantage that it produces a one-piece connection between the first section or the actuating element and the tool, which leads to a particularly fixed connection and an efficient force transmission between the two components. A control rod is also simple and inexpensive to produce.

In a further embodiment of the invention, the first section and the second section are connected by means of a swivel axis.

Although it is possible to connect the first section and the second section by means of any flexible component, such as a helical spring for example, a swivel axis is a preferred embodiment, since this provides a fixed connecting point between the two components. The articulation of the second section consequently takes place at a precisely defined point.

The fact that a fixed connection between the first section and the second section is provided by a swivel axis also means that the force transmission from the actuating element to the second section is made more efficient, since such a connection has no further degrees of freedom in the direction of which the articulating section could deviate.

In an embodiment of the invention, the tool is arranged movably about a pivot axis on the second section.

In a way similar to the arrangement of the first section and the second section about a swivel axis, the arrangement of the tool about a pivot axis is a particularly fixed connection between the tool and the second section. As a result, the force transmission from the control element to the tool is also made particularly effective, since the tool once again has no further possibilities to deviate.

In a further embodiment of the measures stated above, the first end of the control element is connected to the first section at a location which lies at a distance from the swivel axis.

Such an eccentric connection of the control element to the first section allows for a circular movement of the second section, and consequently of the tool attached to it, in relation to the first section to be converted into a linear movement in a simple manner. During the articulation, the control element and the second section move on circular paths around two eccentric centre points. This causes changes in the distance between the two circular paths, described by the control element and the second section.

Since the control element now has a fixed length, the distance of the first end, and consequently the distance of a second end, of the control element from a given point on the second section changes during the articulation. This linear relative movement between the control element and the second section can be used for moving the tool back and forth between an open position and a closed position.

In a further embodiment of the measure stated above, a second end of the control element is connected to the tool at a location which lies at a distance from the pivot axis.

An eccentric arrangement of the control element with respect to the swivel axis which connects the first section to the second section has the effect, as described above, of causing a linear relative movement between that point of the second section and the control element. Consequently, a linear relative movement is also caused between the pivot axis, by which the tool is arranged on the second section, and the control element.

In the case of a connection of the actuating element to the first end of the control element, apart from its circular movement the control element performs a linear movement, since its fastening point is located on the linearly moving actuating element. Consequently, the centre point of the circular movement of the control element performs a linear relative movement in relation to the swivel axis, and consequently in relation to every point on the second section. The combination of the linear movement of the fastening point and the circular movement of the control element leads to a linear relative movement of the second end of the control element with respect to the second section and consequently also in relation to the pivot axis fixedly connected to the second section.

If the second end of the control element is then connected to the tool at a location which lies at a distance from the pivot axis, a linear movement of the control element in relation to the second section leads to the connecting location between the control element and the tool moving in relation to the pivot axis. This linear movement is converted by this eccentric arrangement into a pivoting movement of the tool with respect to the second section. This allows the tool to be moved by the control element back and forth between an open position and a closed position in a simple way.

In a further embodiment of the invention, the control element is connected by means of a ball joint at the first end to the first section or to the actuating element or at the second end to the tool.

A ball socket as a mating component for a ball represents an articulated connection of two components which is simple to produce in production engineering terms but is reliable.

Furthermore, the use of a ball socket produces only a few corners and undercuts, which are difficult to clean and in the long term could lead to accumulations of bacteria in the instrument.

In a further embodiment of the invention, the control element is designed at least in a region of the second end as a toothed rack which is in operative connection with the tool by means of a gear mechanism.

The combination of a toothed rack and a gear mechanism leads to a particularly secure connection, by the engagement of gear wheels in the toothed rack, and consequently to a very effective force transmission.

In a further embodiment of the invention, the instrument is designed as a retractor.

The combination of an articulated section and a tool which has an open position and a closed position has proven to be advantageous in particular for use in the case of retractors, since for example an organ can be gripped from the rear side and manipulated by the articulating section.

The tool with an open position and a closed position has the advantage that a small cross section of the endoscopic instrument is created, for example by placing various retractor fingers one over the other during insertion in the closed position, so that it can be inserted easily through small incisions even into regions of the body of a patient that are accessible only with difficulty.

In the open position in turn, the tool then offers a large supporting surface, so that the force exerted when an organ is being manipulated is distributed over a large area, whereby damage to the organ caused by overloading at single points is avoided.

In a further embodiment, the retractor comprises at least two retractor fingers, it being possible for these to form a cross or a fan in an open position of the tool.

The arrangement of at least two retractor fingers which form a cross in the open position has the advantage that, even with two retractor fingers, the force applied to the retractor can be distributed over a large surface area. Consequently, a large effective supporting surface can be created with only a few components.

Configuring the retractor fingers in such a way that they form a cross in the open position also has the advantage that such a cross can be symmetrically designed, the point of application for an applied force being located approximately at the centre of the cross. This ensures that the force is distributed uniformly over the entire retractor fingers.

Forming the retractor fingers in such a way that they form a fan in the open position has the advantage that a continuous supporting surface is thereby created in this way, so that possible injuries caused by tissue penetrating into intermediate spaces between the retractor fingers are minimized.

It is understood that the above features and features described below can be used not only in the combinations specified but also in other combinations or in isolation without departing from the scope of the present invention.

BRIEF DESCRIPTION OF THE DRAWINGS

The invention is described in more detail and explained below on the basis of selected exemplary embodiments in conjunction with the accompanying drawings, in which.

DETAILED DESCRIPTION OF PREFERRED EMBODIMENTS

Figure 1:
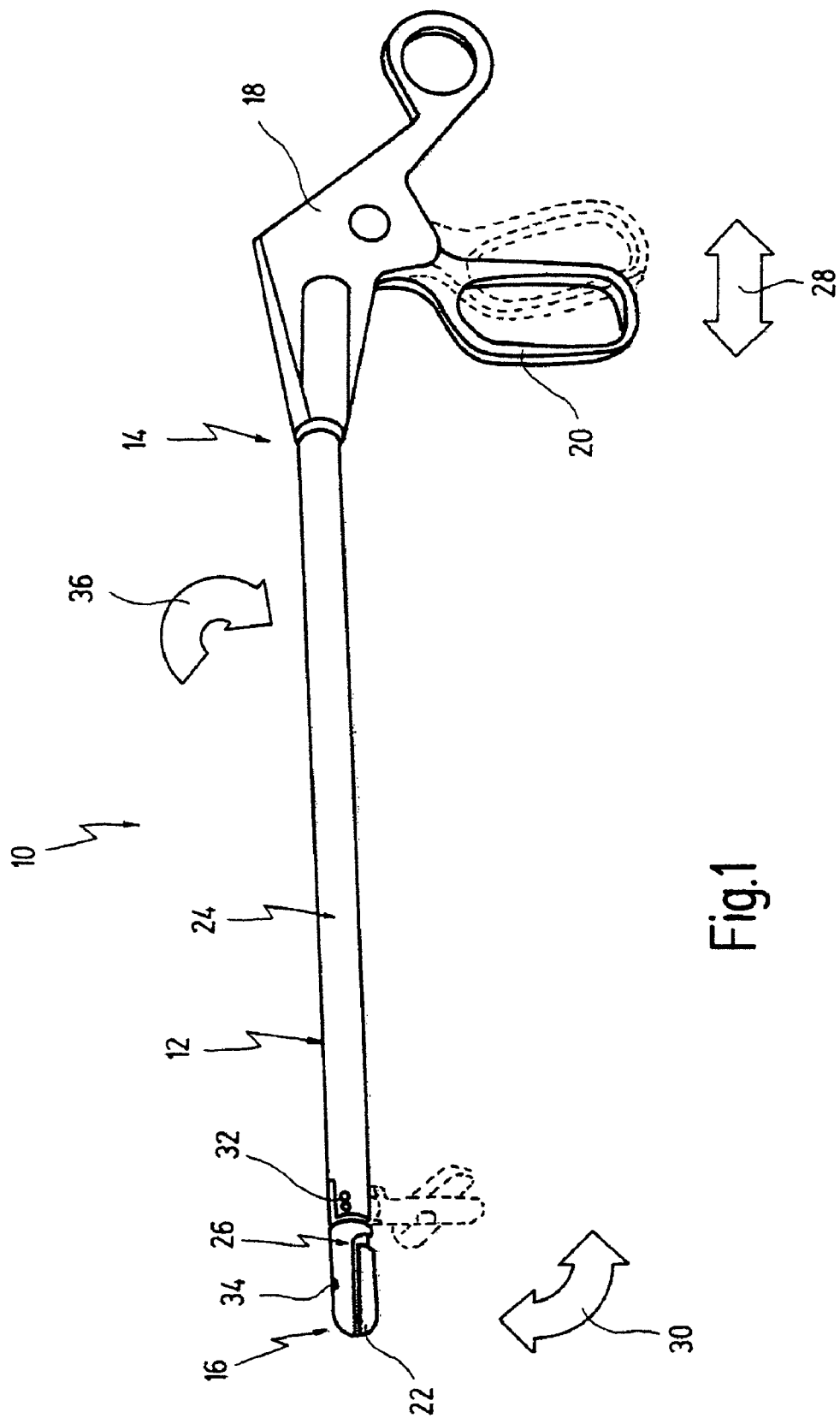
FIG. 1 shows a perspective view of a first embodiment of an endoscopic retractor according to the invention, having the first section and the tool connected via a control element.

In the foregoing description of the drawings and in the following description, the expression "closed position" means that the second section is not articulated with respect to the first section, and the tool is in the closed position. The expression "open position" means that the second section is articulated with respect to the first section, and the tool is in an open position.

In FIGS. 1 to 10, an endoscopic instrument is denoted in its entirety by the reference numeral 10. It is in this case an endoscopic retractor.

This instrument 10 has a shaft 12 with a proximal end 14 and a distal end 16. Arranged at the proximal end 14 of the shaft 12 is a grip 18, which has a handle 20.

The grip 18 shown here is a scissors-like grip, the handle 20 likewise being designed as a scissors-like grip.

Arranged at the distal end 16 of the shaft 12 is a tool, which is designed here as a pivoting cross 22.

The shaft 12 also has a first section 24 and a second section 26, which can be articulated with respect to the first section 24.

Inside the shaft 12 there also runs an actuating element (not shown here), which connects the second section 26 to the handle 20. If the handle is then displaced to the right in the direction of the double-headed arrow 28 into the position represented by broken lines, the actuating element in the shaft 12 is displaced in the distal direction.

This displacement has the effect that the second section 26 is articulated downwards by 90° in the direction of the double-headed arrow 30 about a swivel axis 32, which is located at the distal end of the first section 24. In the process, the pivoting cross 22 is pivoted by 90° with respect to the second section 26 about a pivot axis 34, which connects the pivoting cross 22 to the second section 26.

Moving the handle to the left in the direction of the double-headed arrow 28, that is back into its starting position, moves the second section upwards in the direction of the double-headed arrow 30, back into its starting position. The pivoting cross 22 is thereby likewise pivoted back into its starting position.

In order to increase the flexibility of an operator, the shaft 12 can also be turned with respect to the grip 18 about its longitudinal axis in the direction of the arrow 36. Such turning allows the position of the second section 26 when it is articulated to be changed in relation to the handle 18, so that the second section when it is articulated for example is not articulated as it is here in the plane of the grip 18 but for example at right angles thereto.

Figure 2:
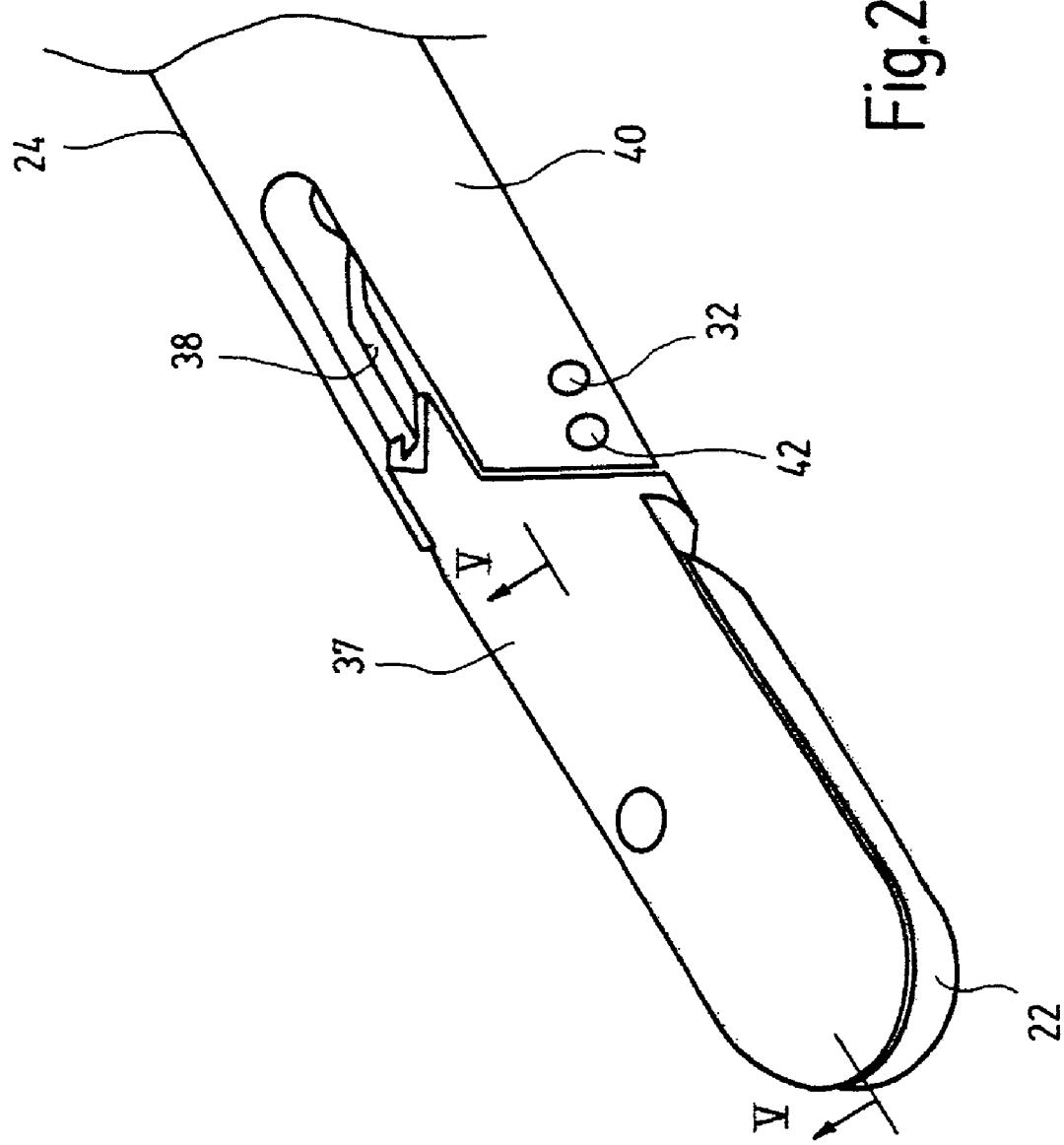
FIG. 2 shows an enlarged perspective view of the distal section of the retractor from FIG. 1 in the closed position.

In FIG. 2, a perspective view of the distal section of the endoscopic instrument 10 from FIG. 1 is shown. It can be seen here that the second section 26 of the shaft 12 is designed as a swivel arm 37. This swivel arm 37 is in operative connection with the distal end of the actuating element 38.

Here, the distal end of the first section 24 of the shaft 12 takes the form of a fork 40, into which the swivel arm 37 is fitted and held there by a pin which forms the swivel axis 32.

Furthermore, the fork 40 has the sleeve 42, which serves the purpose of connecting the first section 24 of the shaft 12 to a control element.

The pivoting cross 22 has at its distal end a rounded-off profile, which together with the distal end of the swivel arm 37 produces the profile of a hemisphere. This hemispherical profile facilitates the atraumatic insertion of the instrument 10 into the body of a patient.

Figure 3:
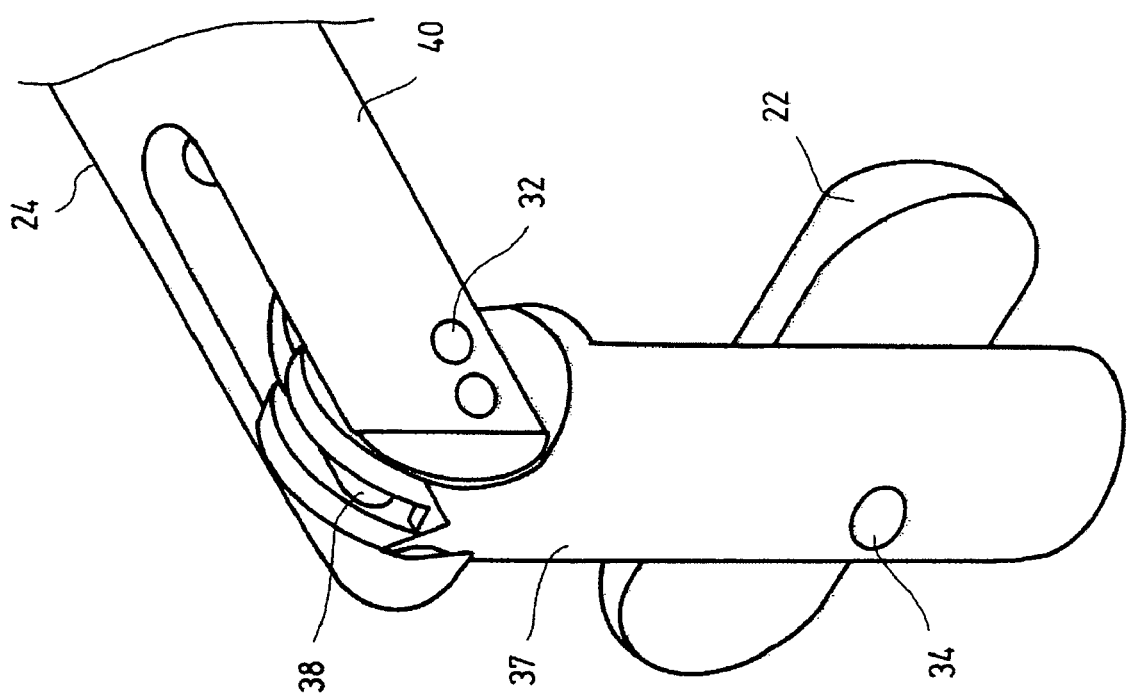
FIG. 3 shows an enlarged perspective view of the distal section of the retractor from FIG. 1 in the open position.

In FIG. 3, the distal section of the instrument 10 is shown in the open position. The actuating element 38 has in this case been displaced in the distal direction in relation to the shaft 12 by actuating the handle 20, as indicated in FIG. 1.

The actuating element 38 is connected to the swivel arm 37 at a location which lies outside the swivel axis 32. This eccentric arrangement has the effect that the linear movement of the actuating element 38 is converted into a circular movement of the swivel arm 34 about the swivel axis 32.

In this representation, the pivoting cross 22 has been pivoted with respect to the swivel arm 37 by 90° about the pivot axis 34. It can be seen here that the pivoting cross 22 has a rounded-off profile on its underside. This profile has the effect of avoiding injuries to the surrounding tissue during the pivoting movement.

Figure 4:
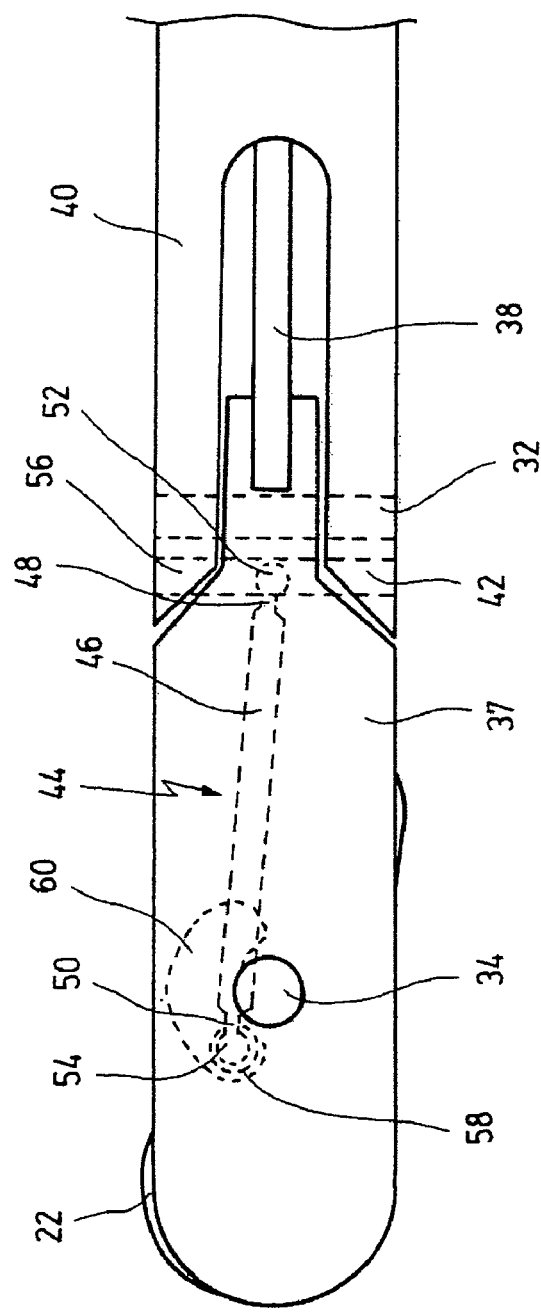
FIG. 4 shows an enlarged plan view of the distal section of the retractor from FIG. 1 in the closed position.

FIG. 4 shows a view of the distal section of the instrument 10, the components located in the instrument 10 being schematically represented by broken lines.

The swivel arm 37 lies inside the fork 40 and is pivotably connected to the latter by means of the pivot axis 32. The swivel arm 37 is also pivotably connected to the actuating element 38. In the swivel arm 37 there runs a control element, which is designed here as a control rod 44. The control rod 44 is substantially symmetrical and has a rod-shaped body 46, which tapers at respectively opposite ends into a neck 48, 50, which is respectively connected to a head which is designed as balls 52, 54.

The ball 52 located at the proximal end of the rod 44 is fixed in place, but mounted such that it is spatially movable in the manner of a ball, in that the sleeve 42 on one side of the fork 40 and a second sleeve 56 on the opposite side of the fork 40 from the sleeve 42 are operatively connected. The ball 54 at the distal end of the control rod 44 lies in a third sleeve 58. This third sleeve 58 is connected in a lower section pivotably, but operatively to the pivoting cross 22 and runs in an upper section in a kidney-shaped milled clearance 60, which extends in an approximately semicircular manner around the pivot axis 34 in the swivel arm 37.

Figure 5:
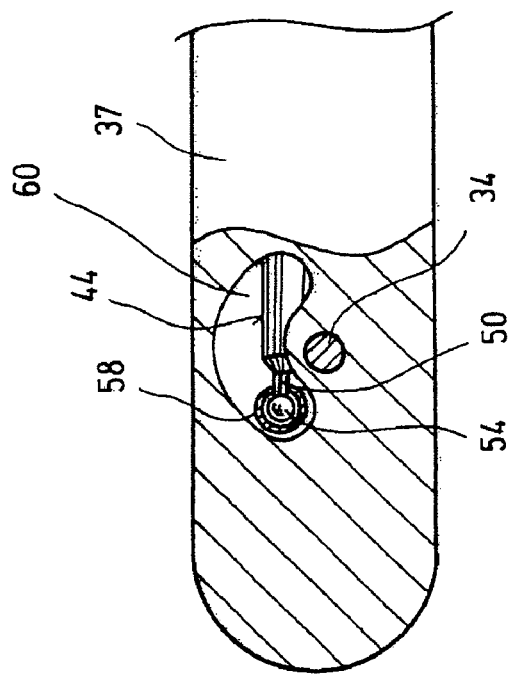
FIG. 5 shows a partial section through the distal section of the retractor from FIG. 1 along the line V-V from FIG. 2.

The third sleeve 58 and the milled clearance 60 can be seen even better in the sectional drawing shown in FIG. 5. Here it can be seen that the ball 54 of the control rod 44 comes to lie in a bore of the sleeve 58, the neck 50 of the control rod 44 being led through a slit in the sleeve 58.

Figure 6:
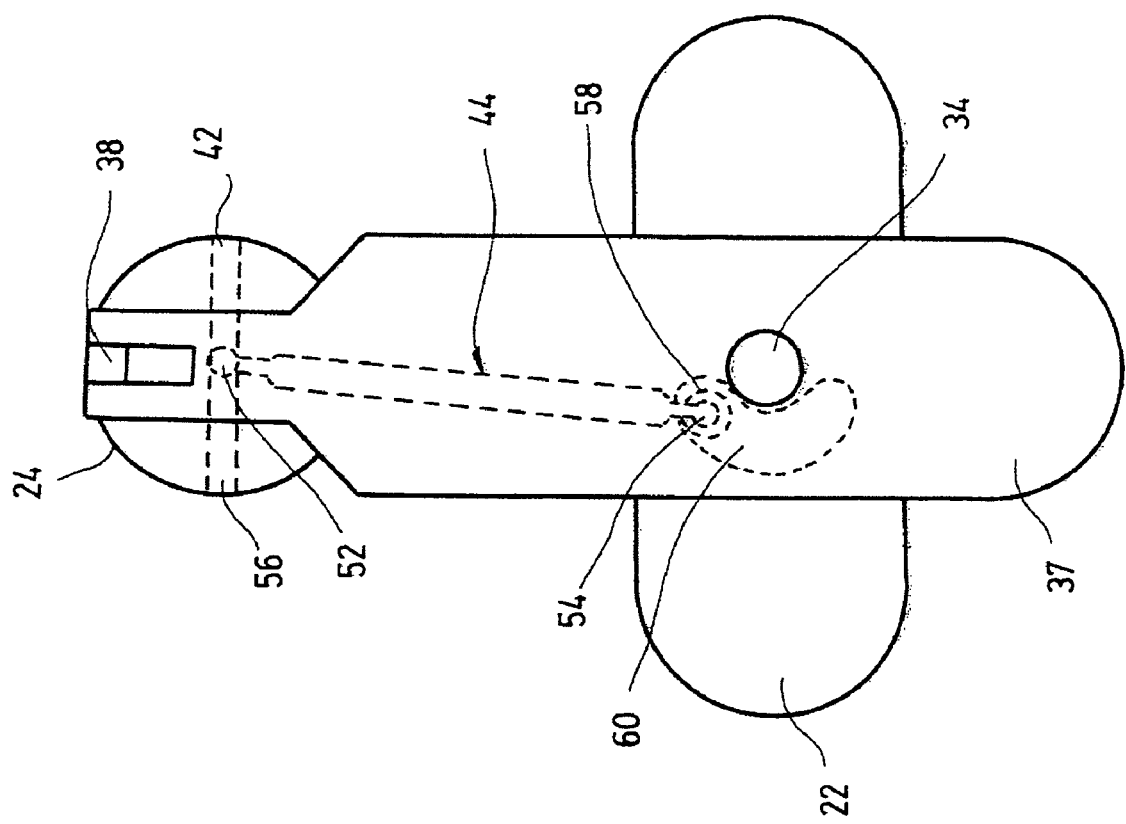
FIG. 6 shows an enlarged frontal view of the distal section of the retractor from FIG. 1 in the open position.

In FIG. 6, a frontal view of the instrument from FIG. 1 is shown in the open position. In order to bring the instrument into this position, the handle 20 was displaced with respect to the grip 18 in the way represented in FIG. 1, whereby the actuating element 38 was displaced in the distal direction in relation to the shaft. The swivel arm 37 is now articulated by 90° with respect to the first section 24 of the shaft 12.

The swivel arm 37 thereby describes a circular path around the swivel axis 32 (not shown here), which lies in the same plane as the two sleeves 42, 56, but in this representation is arranged offset into the plane of the paper.

At the same time as the circular movement of the swivel arm 37, the control rod 44 performs a circular movement about an axis which is defined by the sleeves 42, 56, which produce the operative engagement between the ball 52, and consequently the control rod 44, and the first section 24.

If the pivot axis 34 is taken as a reference point for a circular movement of the swivel arm 37, a first circular path is defined in this way. A second circular path is defined by the control rod 44 with the ball 54 describing a circular path whose centre point is formed by the ball 52.

Since the circular path of the pivot axis 34 has a different centre point than the circular path of the ball 54, the distance between the ball 54 and the pivot axis 34 changes during the movement of the swivel arm 37. The distance between the pivot axis 34 and the ball 54 becomes shorter until the ball 54 is offset to the rear, seen from distal to proximal in the direction of the instrument. The ball 54 and the sleeve 58, in which the latter is held with non-positive engagement, thereby move in the milled clearance 60 of the swivel arm 37. Since the sleeve 58 is operatively connected to the pivoting cross 22, the pivoting cross is articulated with respect to the swivel arm 37 along the path predetermined by the milled clearance 60 and is pivoted by an angle of 90° with respect to the swivel arm 37.

Figure 7:
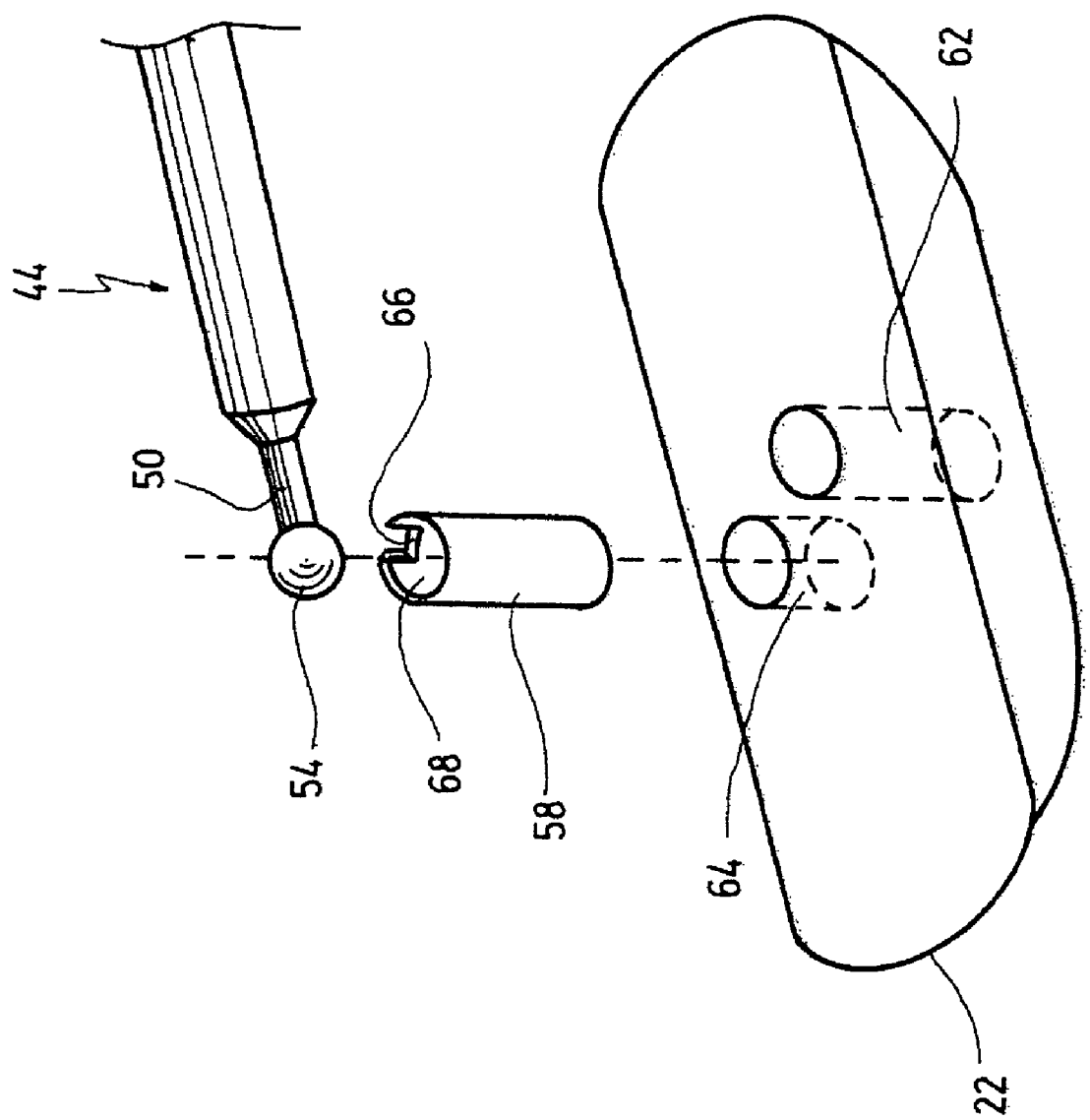
FIG. 7 shows an enlarged exploded representation of the connection between the tool and the control element of the retractor from FIG. 1.

In FIG. 7, the pivoting cross 22 is shown in more detail. The pivoting cross 22 has a central bore 62, which serves for receiving the pivot axis. Offset with respect to the bore 62, a further bore 64 is provided in the pivoting cross 22. This bore 64 is a blind bore.

Fitted in this blind bore is a sleeve 58. Although it is possible to configure the bore 64 as a through-bore, a blind bore is to be preferred, since this makes it possible without a further holding device for the sleeve 58 to be fitted in such a way that it does not fall out of the pivoting cross.

The distal section of the control rod 44 is fitted into the sleeve 58, the distal neck 50 coming to lie in a slit 66 of the sleeve 58 and the ball 54 at the distal end of the control rod 44 coming to lie in the bore 68 of the sleeve 58.

This structural design has the effect that the control rod 44 is connected operatively to the pivoting cross 22, but is still freely pivotable with respect to the centre point of the bore 64.

If the pivoting cross 22 is then held in the section of the first bore 62 and a pushing or pulling force is exerted on the control rod 44 connected operatively to the pivoting cross 22, the sleeve 58, and consequently the bore 64, is moved on a circular path around the first bore 62, and consequently the pivoting cross 22 pivots about the bore 62 or a pivot axis 34 possibly to be fitted into it.

Figure 8:
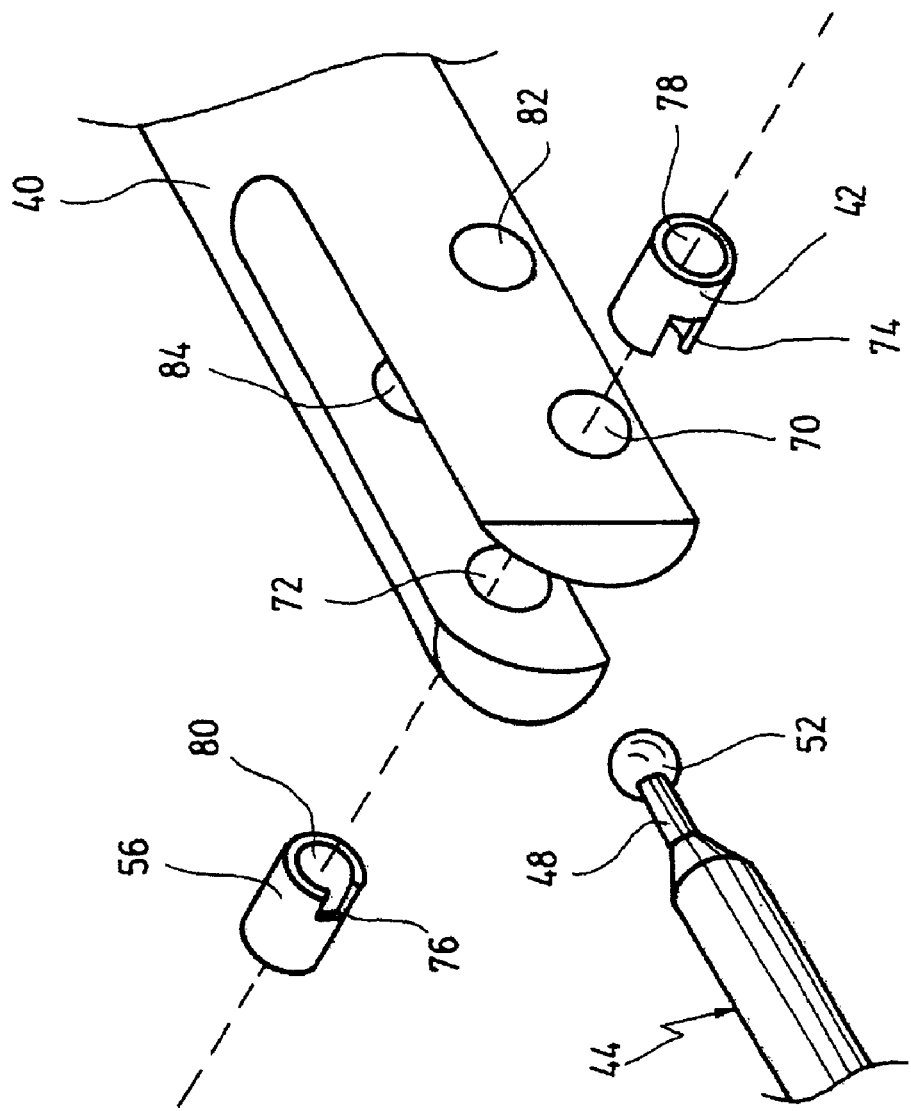
FIG. 8 shows an enlarged exploded representation of the connection between the distal section and the control element of the retractor from FIG. 1.

In FIG. 8, the fork 40 which forms the distal end of the shaft 12 is shown. This fork 40 has at the distal end two aligned bores 70, 72. The sleeves 42, 56 can be inserted into these bores 70, 72. The control rod 44 is then inserted with its proximal end into the fork 40, so that the ball 52 is aligned with the bores 70, 72. After that, the sleeves 42, 56 are inserted through the bores 70 and 72, respectively. The sleeves 42, 56 thereby enclose the ball 52, the sleeve 42 having a slit 74 and the sleeve 56 having a slit 76, which can be brought into alignment with each other. The neck 48 of the control rod 44 comes to lie in a wide slit designed by the slits 74, 76, and the ball 52 comes to lie in the bore 78 of the sleeve 42 and the bore 80 of the sleeve 56. Consequently, the control rod 44 is connected to the fork 40 operatively, but pivotably about an axis which is formed by the centre axis of the bore 70 and 72.

The fork 40 also has the bores 82, 84, which are in alignment with each other and are provided for receiving the swivel axis 34 for the swiveling of the swivel arm 37.

Figure 9:
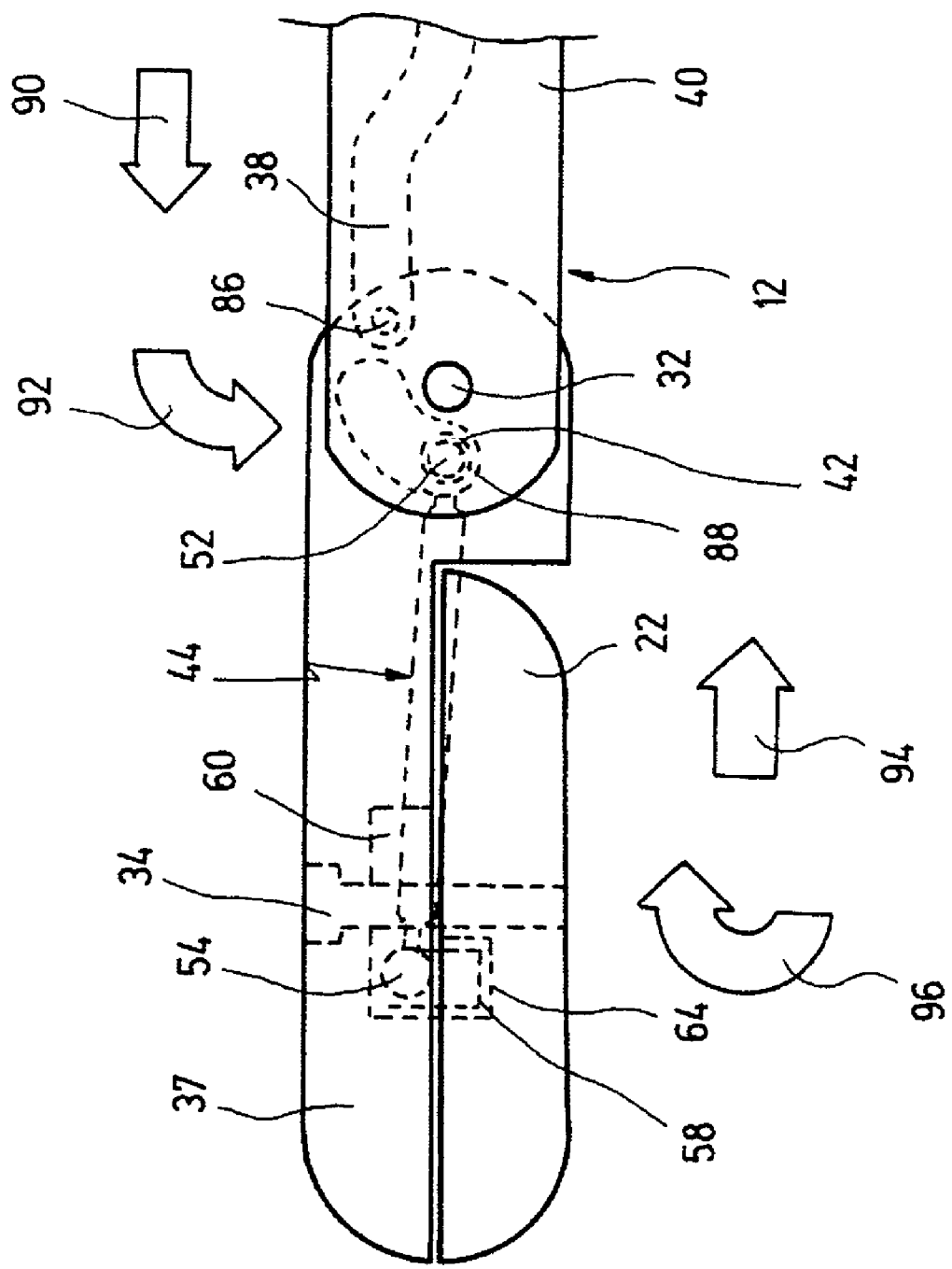
FIG. 9 shows an enlarged side view of the distal section of the retractor from FIG. 1 in the closed position.

In FIG. 9, a side view of the distal section of the instrument 10 from FIG. 1 is shown, the internal mechanical components being represented by broken lines. Here, the swivel arm 37 is connected to the fork 40 pivotably about the axis 32. The swivel arm 37 is also movably connected to the actuating element 38 by a pin 86.

It is also clear from this representation that the swivel arm 37 has a further kidney-shaped milled clearance 88, in which the sleeves 42, 56 and the ball 52 arranged at the proximal end of the control rod 44 are received.

It can also be seen in this drawing that the sleeve 58 comes to lie partly in the bore 64 of the pivoting cross 22 and partly in the milled clearance 60 of the swivel arm 37. The pivot axis 34 is designed here as a rivet.

If the handle 20 of the instrument 10 is then actuated, the actuating element 38 is displaced in relation to the shaft 12 in the distal direction, that is in the direction of the arrow 90. As a result, a pushing force is exerted in the same direction on the pin 86, which connects the actuating element 38 to the swivel arm 37.

This pushing force has the effect that the pin 86 is displaced on a circular path around the pivot axis 32, whereby the swivel arm 37 performs a swiveling movement in the direction of the arrow 92. This swiveling movement has the effect that the pivot axis 34 moves on a circular path around the swivel axis 32. Furthermore, the swivel arm 37 moves over the kidney-shaped milled clearance 88 around the sleeves 42, 56 and the ball 52 of the control rod 44.

The position of the ball 52 in relation to the fork 40 or in relation to the swivel axis 32 remains unchanged when this happens. Since the swivel axis 34 is in operative connection with the pivoting cross 22 and this pivoting cross 22 is in operative connection with the ball 54, the ball 54 is led around the ball 52 on a circular path. Therefore, two eccentric circular movements are involved here.

With such eccentric circular movements, the relative position of the circular paths with respect to each other changes, that is in this case the relative position of the ball 54 of the control rod 44 with respect to the pivot axis 34 of the swivel arm 37 changes. The ball 54 of the control rod 44 is hereby offset in relation to the pivot axis 34 of the swivel arm 37 in the direction of the arrow 94 towards the axis 32.

This relative movement of the ball 54 has the effect of exerting a pulling force via the sleeve 58 and the bore 64 on the pivoting cross 22. This pulling force moves the ball 54 on a circular path around the pivot axis 34, whereby the pivoting cross 22, which is operatively connected to the ball 54, performs a pivoting movement about the pivot axis 34 in the direction of the arrow 96.

Figure 10:
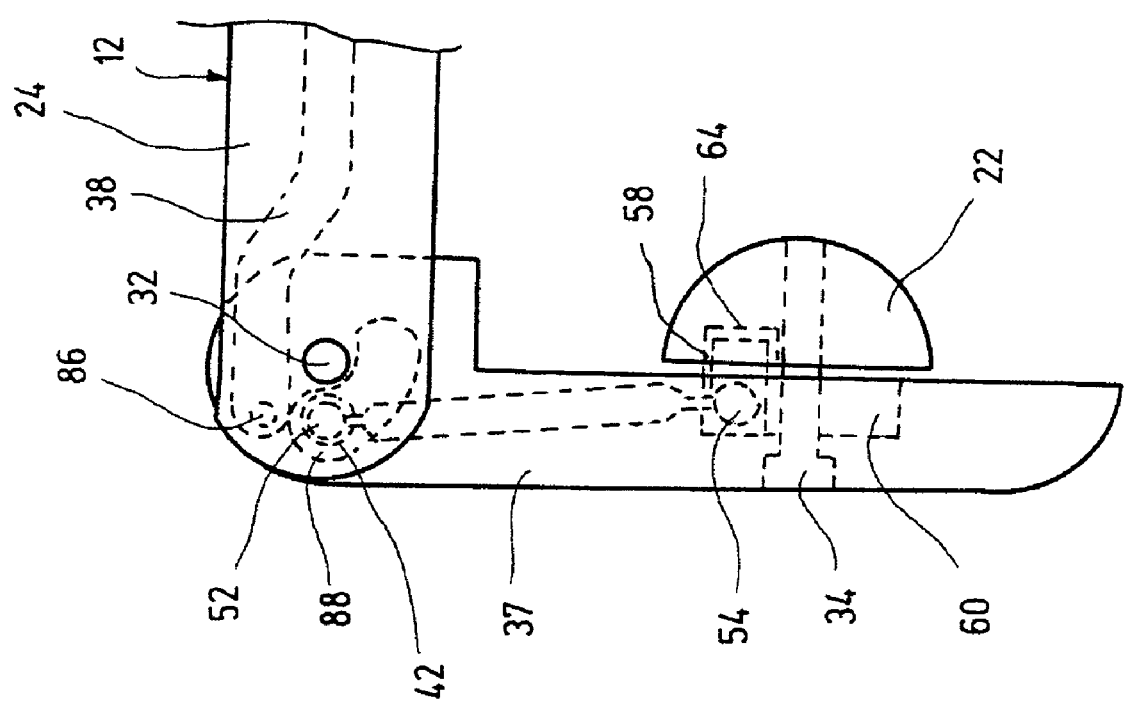
FIG. 10 shows an enlarged side view of the distal section of the retractor in FIG. 1 in the open position.

FIG. 10 shows the same view as FIG. 9, but in the open position of the endoscopic instrument 10. It can be seen here that the ball 54 is offset with respect to the pivot axis 34 in the milled clearance 60. The pulling force thereby exerted on the sleeve 58, and consequently the bore 64, has pivoted the pivoting cross 22 with respect to the swivel arm 37 by 90° about the pivot axis 34.

It can also be seen that the milled clearance 88 has moved around the ball 52 and the sleeve 42.

In this open position, both the swivel arm is angled and the pivoting cross is articulated with respect to the swivel arm.

In this position, the retractor can be used, for example in a minimally invasive operation, to grasp an organ, for example the liver, from behind and move it, in order for example to make an examination of the rear side of the liver possible.

Figure 11:
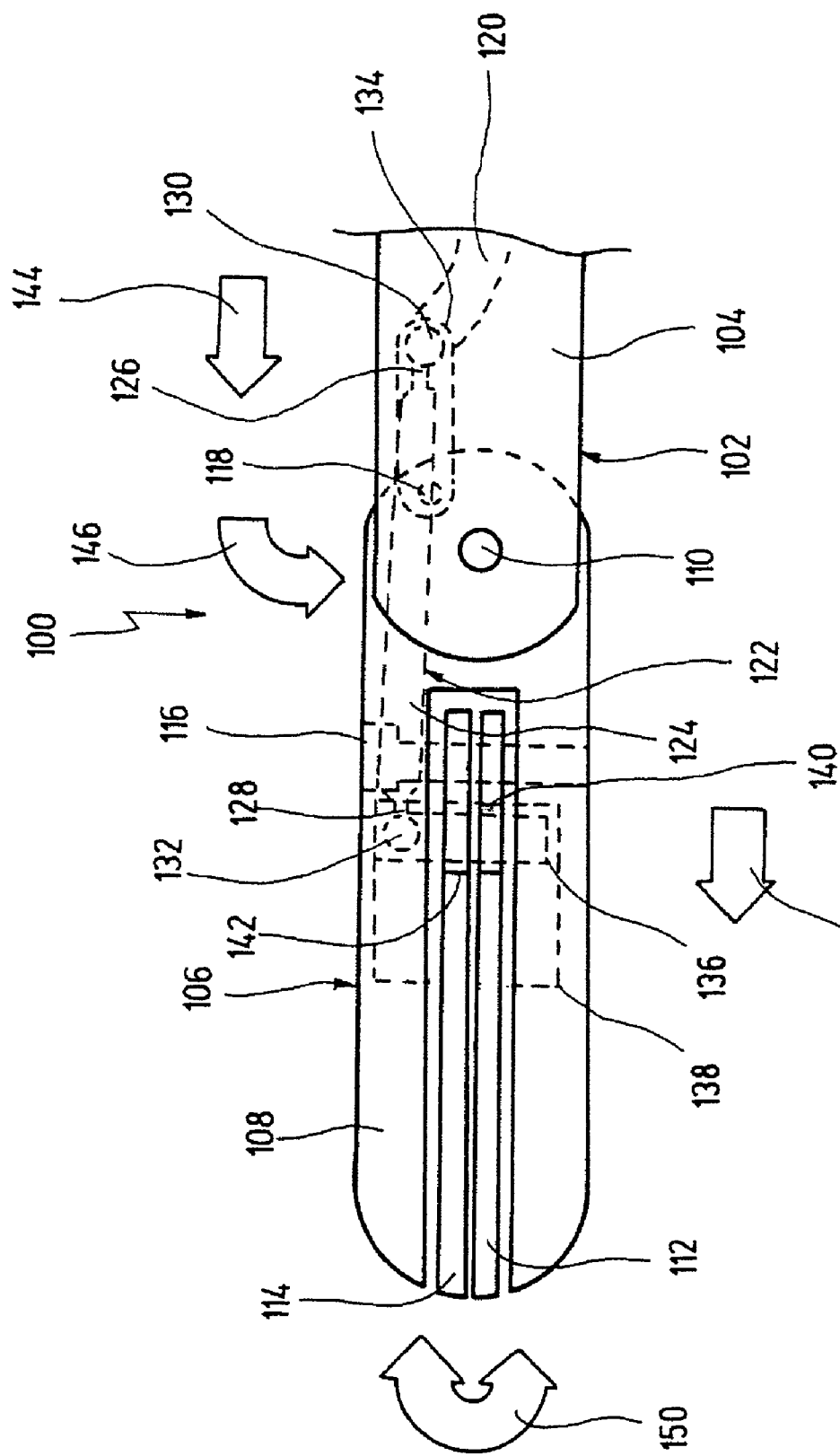
FIG. 11 shows an enlarged side view of the distal section of a second embodiment of a retractor according to the invention in the closed position, the retractor hereby having the actuating element and the tool connected via a control element.

In FIG. 11, a side view of a distal section of a further embodiment of an endoscopic retractor is shown, the internal mechanical components being represented by broken lines.

Here, the endoscopic retractor has a shaft 100, which has a first section 102, which is designed here as a fork 104, and a second section 106, which is designed here as a swivel arm 108.

The swivel arm 108 lies in the distal end of the fork 104 and is pivotably connected to the latter by means of a swivel axis 110, which here takes the form of a pin.

A tool of the endoscopic retractor that is arranged on the second section 106 of the shaft 100 here takes the shape of a fan, which has retractor fingers 112 and 114. The retractor fingers 112, 114 are mounted pivotably in the swivel arm 108 by means of a swivel axis 116, which is designed here as a screw. The distal end of the swivel arm 108 and the distal ends of the retractor fingers 112 and 114 are rounded off here and form an approximately hemispherical profile, which makes the atraumatic insertion of the instrument into the body to the greatest extent possible.

At its proximal end, the swivel arm 108 is also connected by a pin 118 to an actuating element 120. The actuating element 120 is connected at its proximal end to a handle in a way analogous to the instrument 10 from FIG. 1 and can be moved axially by means of this handle.

An axial movement of the actuating element 120 has the effect of causing an articulation of the swivel arm 108 with respect to the fork 104. For this purpose, the pin 118 is located in an eccentric position with respect to the swivel axis 110. If the actuating element 120 is then moved in an axial direction, the pin 118 performs a circular movement around the swivel axis 110, whereby the swivel arm 108 is articulated with respect to the fork 104.

The actuating element 120 is also connected to a control element, which is designed here as a control rod 122. The control rod 122 is substantially symmetrical and has a rod body 124, which tapers respectively in the direction of its proximal and distal ends to a rod neck 126 and 128, respectively.

The rod necks 126, 128 are adjoined proximally and distally by heads of the control rod 122, which are designed here as balls 130 and 132, respectively.

The ball 130, located at the proximal end of the control rod 122, lies in a slit sleeve 134, which is connected fixedly, but pivotably, to the actuating element 120, the proximal neck 126 of the control rod 122 coming to lie in a slit of the sleeve 134.

The ball 132 at the distal end of the control rod 122 comes to lie in a slit sleeve 136. This slit sleeve 136 is displaceably arranged in a milled clearance 138 in the swivel arm 108. The slit sleeve 136 is also displaceably arranged in with respect to the milled clearance 138 of the swivel arm 108 obliquely arranged milled clearances 140 and 142 in the retractor fingers 112 and 114, respectively. The ball 132 at the distal end of the control rod 122 thereby comes to lie in the sleeve 136, while the rod neck 128 at the distal end of the control rod 122 comes to lie in a slit of the sleeve 136.

If the actuating element 120 is then moved with the aid of the handle (not shown here) in the direction of the arrow 144 from proximal to distal in the direction of the shaft 100, the pin 118 describes a circular path around the swivel axis 110 in the direction of the arrow 146. This causes an articulation of the swivel arm 108 with respect to the fork 104, likewise in the direction of the arrow 146.

The fact that the control rod 122 is fixedly connected to the actuating element 120 by means of the sleeve 134 and the ball 130 has the effect that the control rod 122 likewise performs a linear movement in the direction of the arrow 148 with respect to the swivel arm 108. As a result, the sleeve 136, fixedly connected to the control rod 122 by means of the ball 132, is displaced in the milled clearance 138 in the distal direction that is likewise in the direction of the arrow 148. The sleeve 136 thereby moves in the with respect to the milled clearance 180 obliquely arranged milled clearances 140 and 142 in the retractor fingers 112 and 114, respectively. This movement has the effect that the retractor fingers 112, 114 are pivoted about the pivot axis 116 with respect to the swivel arm 108 in the direction of the double-headed arrow 150 in respectively opposite directions.

Figure 12:
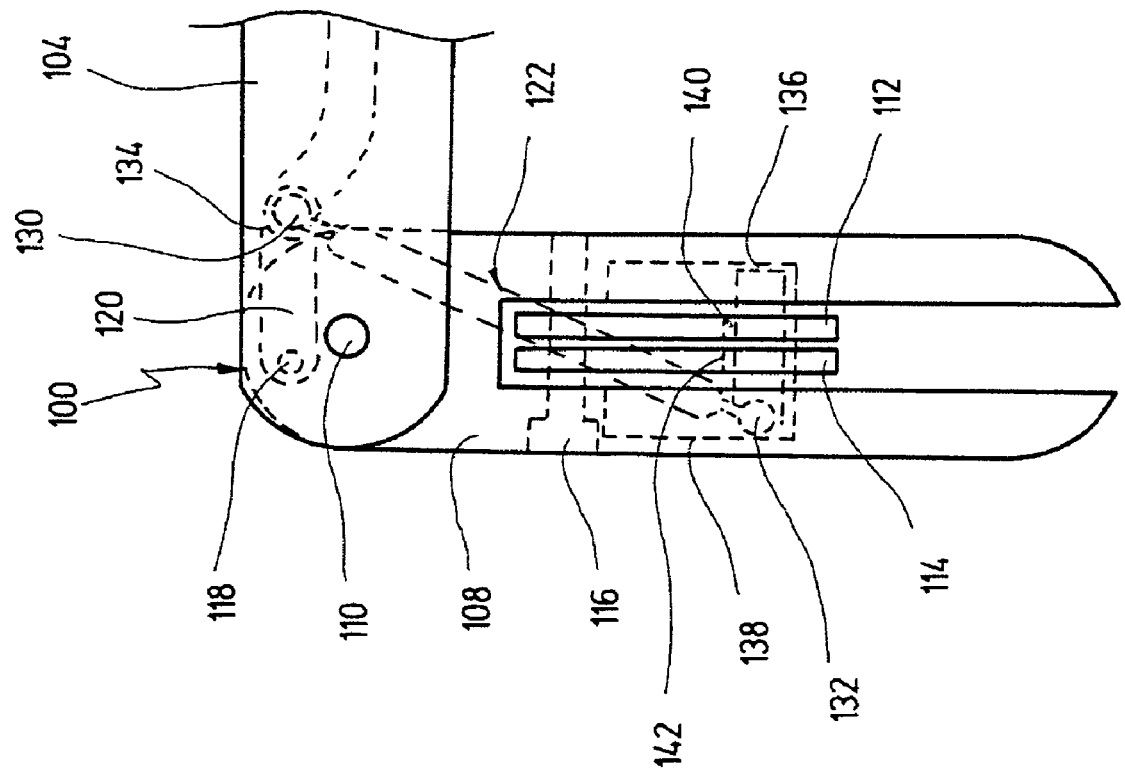
FIG. 12 shows an enlarged side view of the distal section of the retractor from FIG. 11 in the open position.

In FIG. 12, the retractor from FIG. 11 is shown in the open position. The actuating element 120 has been displaced for example with respect to the swivel axis 110 in the direction of the distal end of the shaft 100. The pin 118 has thereby performed a circular movement around the swivel axis 110, whereby the swivel arm 108 has been articulated at an angle of 90° with respect to the fork 104.

The sleeve 134, and thereby the ball 130, at the proximal end of the control rod 122 have likewise been displaced with respect to the swivel axis 110 in the distal direction. Furthermore, the ball 132 at the distal end of the control rod 122, since it is fixedly connected to the swivel arm 108, has performed a circular movement around the ball 130 at the proximal end of the control rod 122 and around the sleeve 134.

This combined linear and circular movement has the effect that the ball 132 at the distal end of the control rod 122 has been displaced in the distal direction with respect to the pivot axis 116. As a result, the sleeve 136 has been displaced in the milled clearance 138 of the swivel arm 108. During this linear movement of the sleeve 136 in the milled clearance 138, the sleeve 136 slides through the oblique milled clearances 140 and 142 of the retractor fingers 112 and 114, respectively, which respectively have bevels in different directions, whereby they were respectively pivoted in different directions about the pivot axis 116 with respect to the swivel arm 108.

Figure 13:
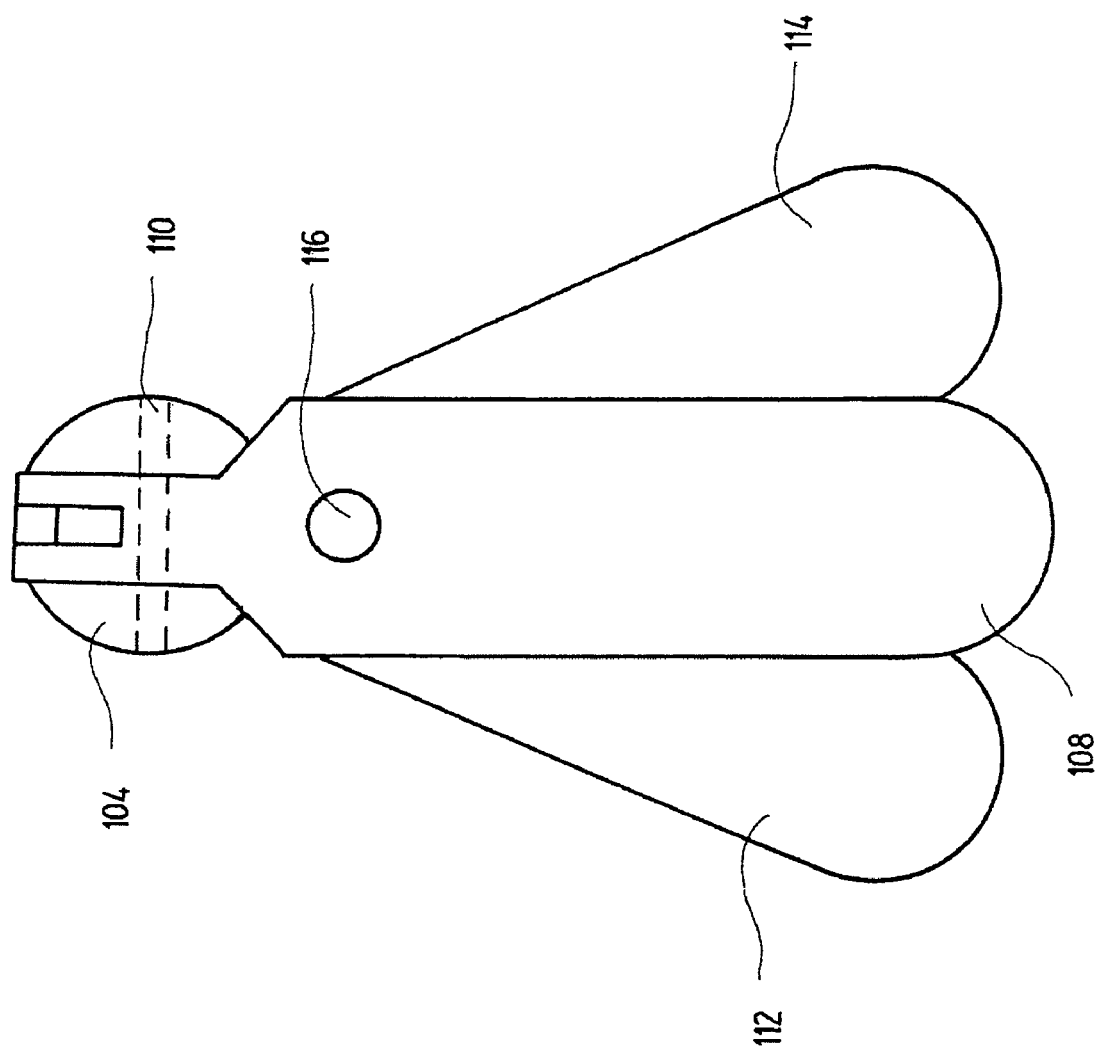
FIG. 13 shows an enlarged plan view of the distal section of the retractor from FIG. 11 in the open position.

FIG. 13 represents this open position once again in plan view. The swivel arm 108 has been articulated with respect to the fork 104 about the swivel axis 110 at an angle of approximately 90°. The retractor fingers 112 and 114 have respectively been pivoted in different directions with respect to the swivel arm 108 about the pivot axis 116. As a result, the swivel arm 108 and the two retractor fingers 112 and 114 assume a fan-shaped configuration.

This configuration has the effect that the supporting surface of the swivel arm 108 is significantly increased, and consequently a force exerted by the swivel arm 108, for example on an organ, is distributed over a significantly larger area, whereby injuries to the organ caused by local overloading are avoided.

What is claimed is:

1. An endoscopic instrument having a shaft comprising a proximal and a distal end,
   a grip comprising a handle being arranged at said proximal end of said shaft and,
   a tool having at least an open position and a closed position, said tool being arranged at said distal end of said shaft,
   said shaft comprising at least two sections, a first section and a second section which can be articulated with respect to said first section,
   said second section comprising said tool,
   said instrument further comprising an actuating element, by means of which said handle is in operative connection with said second section, whereby an articulation of said second section can be initiated with said actuating element,
   said first section and said tool being connected by a control rod, having a first end and a second end, said first end and said second end each comprising a neck received in a slit of a sleeve and a ball received in said sleeve, by means of which control rod said tool is moved back and forth between said closed position and said open position in a course of said articulation of said second section,
   such that a simultaneous articulation of said second section and a movement between said open position and said closed position of said tool is accomplished by the movement of said actuating element.

2. The instrument of claim 1, wherein said first section and said second section are connected by means of a swivel axis.

3. The instrument of claim 2, wherein said first end of said control rod is connected to said first section at a location which lies a distance from said swivel axis.

4. The instrument of claim 1, wherein said tool is arranged movably about a pivot axis on said second section.

5. The instrument of claim 4, wherein said second end of said control rod is connected to said tool at a location which lies at a distance from said pivot axis.

6. The instrument of claim 1, wherein said instrument is designed as a retractor.

7. The instrument of claim 6, wherein said retractor comprises at least two retractor fingers.

8. The instrument of claim 7, wherein, in said open position of said tool, said retractor fingers form a cross.

9. The instrument of claim 1, wherein said instrument is designed as a retractor comprising at least two retractor fingers, wherein, in said open position of said tool, said retractor fingers form a fan.

10. An endoscopic instrument having a shaft comprising a proximal and a distal end,
    a grip comprising a handle being arranged at said proximal end of said shaft and,
    a tool having at least an open position and a closed position, said tool being arranged at said distal end of said shaft,
    said shaft comprising at least two sections, a first section and a second section which can be articulated with respect to said first section,
    said second section comprising said tool,
    said instrument further comprising an actuating element, by means of which said handle is in operative connection with said second section, whereby an articulation of said second section can be initiated with said actuating element,
    said actuating element and said tool being connected by a control rod, having a first end and a second end, said first end and said second end each comprising a neck received in a slit of a sleeve and a ball received in said sleeve, by means of which control rod said tool is moved back and forth between said closed position and said open position in a course of an articulation of said second section, such that a simultaneous articulation of said second section and a movement between said open position and said closed position of said tool is accomplished by a movement of said actuating element.

11. The instrument of claim 10, wherein said second section and said actuating element are connected by means of a swivel axis.

12. The instrument of claim 11, wherein said first end of said control element is connected to said actuating element at a location which lies at a distance from said swivel axis.

13. The instrument of claim 10, wherein said tool is arranged movably about a pivot axis on said second section.

14. The instrument of claim 13, wherein said second end of said control rod is connected to said tool at a location which lies at a distance from said pivot axis.

15. The instrument of claim 10, wherein said instrument is designed as a retractor.

16. The instrument of claim 15, wherein said retractor comprises at least two retractor fingers.

17. The instrument of claim 16, wherein in said open position of said tool said retractor fingers form a cross.

18. The instrument of claim 10, wherein said instrument is designed as a retractor comprising at least two retractor fingers, wherein in said open position of said tool said retractor fingers form a fan.

* * * * *